United States Patent [19]

Knosp

[11] 4,062,676

[45] Dec. 13, 1977

[54] GOLD ALLOY FOR FIRING ON PORCELAIN FOR DENTAL PURPOSES

[75] Inventor: Helmut Knosp, Pforzheim, Germany

[73] Assignee: Deutsche Gold- und Silber-Scheideanstalt Vormals Roessler, Frankfurt, Germany

[21] Appl. No.: 702,729

[22] Filed: July 6, 1976

[51] Int. Cl.² .............................................. C22C 5/02
[52] U.S. Cl. .................................................... 75/165
[58] Field of Search ......................................... 75/165

[56] References Cited

U.S. PATENT DOCUMENTS

| | | | |
|---|---|---|---|
| 1,987,452 | 1/1935 | Taylor | 75/165 |
| 2,980,998 | 4/1961 | Coleman et al. | 75/165 X |
| 3,413,723 | 12/1968 | Wagner et al. | 75/165 |
| 3,666,540 | 5/1972 | Burnett | 75/165 X |

FOREIGN PATENT DOCUMENTS

| | | | |
|---|---|---|---|
| 1,134,520 | 8/1962 | Germany | 75/165 |
| 2,424,575 | 12/1975 | Germany | 75/165 |
| 957,493 | 5/1964 | United Kingdom | 75/165 |

*Primary Examiner*—C. Lovell
*Attorney, Agent, or Firm*—Cushman, Darby & Cushman

[57] ABSTRACT

Gold alloys for firing on porcelain for dental purposes are prepared from 60 to 90 weight % gold, 5 to 35 weight % platinum, 0.1 to 3 weight % indium, 0 to 10 weight % palladium, 0.5 to 3 weight % rhodium, 0 to 3 weight % tin, 0.1 to 2 weight % tantalum and/or tungsten and 0.3 to 2 weight % zinc, the weight ratio of the platinum group metals to zinc to tantalum and/or tungsten are 15–30:1:0.5–1.3.

11 Claims, No Drawings

GOLD ALLOY FOR FIRING ON PORCELAIN FOR DENTAL PURPOSES

The invention is directed to a yellow gold alloy suitable for firing thereon of porcelain for dental purposes which, besides gold, platinum, indium, tin and rhodium, also includes zinc and tantalum and/or tungsten.

In the dental prosthesis, it is customary to cover crowns and bridges of special noble metal alloys with porcelain. The prominent idea is to combine the good mechanical properties of the alloy and the aesthetic appearance and the tissue compatability or porcelain.

In the infancy of this art, it was tried to fire ceramic composition on caps and structures of platinum-iridium alloys. Because of the poor workability of these high melting alloys and the incomplete harmonization of the properties with those of the porcelain, however, there very frequently occur failures.

In the past years, a series of special alloys have become known which, based on their physical and mechanical properties, substantially satisfy the requirements of the firing on art. There are used alloys which contain 70 to 90% gold, 5 to 15% platinum, 0.5 to 10% palladium, 0.1 to 2% indium, 0.1 to 2% tin, as well as small additions of silver, copper, iron, iridium and rhenium.

All of these alloys, however, have the disadvantage that they show a gray color. However, in dental gold alloys a yellow gold color is very much desired. Especially in visible, non-faced parts of a metal structure finished by a fired on alloy a yellow color is desired for aesthetic reasons. Also, at those places of the structure on which the ceramic is molded somewhat thinly a living appearance is caused by a yellow color. Therefore, in recent years, there have not lacked attempts to produce alloys for firing on which are considerably yellower in color then those previously known and simultaneously conform to the necessary industrial requirements in their physical and mechanical properties.

There are known alloys which besides the above-mentioned constituents also contain nickel, titanium and zinc, as well as large amounts of copper. Besides it was tried to attain a deepening of the yellow gold color by increasing the gold content and lowering the palladium content. However, all of these procedures can merely produce alloys which only come a little nearer the yellow gold color than the previous customary firing on alloys. It has further been found that the properties of the alloys are unfavorably influenced through the named additives. For example, titanium causes a slag formation in melting and casting because of the high negative formation enthalpy of its oxide, copper and, particularly, zinc very strongly lower the solidus temperature so that there can no longer be guaranteed a sufficient heat resistance of the alloy during the firing on of the porcelain.

Furthermore, there are known gold alloys which besides gold, platinum, iridium, indium and tin also contain rhodium and/or tantalium and/or tungsten, wherein the tantalum and tungsten cause an intensification of the gold color. The alloys, however, have the disadvantage that in repeated meltings and castings of the alloys, the deep gold color fades.

Therefore, it was the problem of the present invention to create yellow gold alloys for the firing on of porcelain for dental purposes which have good mechanical properties and a deep gold color and which also remain after repeated meltings and castings.

This problem was solved according to the invention by using gold alloys which besides 60 to 90 weight % gold, 5 to 35 weight % platinum, 0 to 10 weight % palladium, 0.1 to 3 weight % indium, 0 to 3 weight % tin, 0.5 to 3 weight % rhodium and 0.1 to 2 weight % tantalum and/or tungsten and also contain 0.3 to 2 weight % zinc, wherein the weight ratio of the sum of the platinum group metals to zinc to tantalum and/or tungsten is 15 to 30:1:0.5 to 1.3. Especially preferred are alloys wherein the corresponding weight ratio is 25:1:1.

Surprisingly, it has been proven that in the gold alloys based on gold-indium-platinum and, optionally, tin there is attained a more or less strong intensification of the gold color by the addition of rhodium and/or tantalum and/or tungsten. The reddish-gold color produced with these additives shows a deepening which even exceeds that obtained with the known copper-containing gold-platinum alloys. Through the addition of 0 to 2 weight % of zinc according to the invention, this intensive gold color remains even after repeated meltings and castings.

By the addition of rhodium, tantalum, tungsten, and zinc, the favorable properties of the alloys to be fired on are not changed substantially. The mechanical properties of hardness, tensile strength, elongation are equal to those of the known fired on alloys and in part even exceed them. An additive of rhodium in combination with tantalum or tungsten or mixtures of tantalum and tungsten, for example, cause a substantial increase in hardness. The solids temperature is sufficiently high. Beyond this clearly advantageous is the lowering of the liquidus temperature caused by the additives of the invention. The thereby limited contraction of the melting range increases the flowability of the alloy melt and acts favorably on the solidification behavior. The adhesiveness of the fired on porcelain is excellent since tantalum and tungsten form an effective adhesive oxide layer. The addition of zinc prevents the oxidation of tantalum and tungsten in the remelting.

Unless otherwise indicated, all parts and percentages are by weight.

Several examples of compositions of alloys with additives of zinc according to the invention are given in the table below. The hardening or tempering was carried out at 600° C. for 15 minutes.

The yellow color of the alloys of the invention even exceeds that of copper containing gold-platinum-cast alloys. Therefore, it is possible to use the alloys of the invention for inlays, crowns and bridges alone or in combination with synthetic resin facings.

The alloys can consist essentially of or consist of the stated materials.

TABLE

| Example | Composition in weight % | | | | | | | | | Melting Range | Vickershardness HV | |
|---|---|---|---|---|---|---|---|---|---|---|---|---|
| | Au | In | Pd | Pt | Rh | Sn | Ta | W | Zn | ° C | Soft | Tempered |
| 1 | 90 | 1.0 | | 5.6 | 3.0 | | 0.1 | | 0.3 | 1100 – 1030 | 75 | 180 |
| 2 | 88 | 1.0 | | 7.9 | 2.5 | | 0.2 | | 0.4 | 1120 – 1035 | 80 | 185 |
| 3 | 86 | 1.5 | 1.9 | 7.1 | 2.9 | | 0.1 | 0.1 | 0.4 | 1130 – 1040 | 90 | 195 |
| 4 | 85 | 0.9 | 7.0 | 5.0 | 0.5 | 0.6 | 0.5 | | 0.5 | 1170 – 1045 | 95 | 198 |

TABLE-continued

| Example | Composition in weight % | | | | | | | | | Melting Range | Vickershardness HV | |
|---|---|---|---|---|---|---|---|---|---|---|---|---|
| | Au | In | Pd | Pt | Rh | Sn | Ta | W | Zn | °C | Soft | Tempered |
| 5 | 80 | 0.5 | 9.5 | 5.5 | 0.5 | 2.0 | 0.8 | 0.2 | 1.0 | 1180 – 1055 | 98 | 200 |
| 6 | 76 | 0.5 | | 18.0 | 0.5 | 2.3 | | 1.5 | 1.2 | 1190 – 1060 | 110 | 210 |
| 7 | 72 | 2.5 | | 21.8 | 0.5 | | | 1.8 | 1.4 | 1200 – 1070 | 115 | 218 |
| 8 | 66 | 3.0 | | 27.0 | 0.5 | | 1.8 | | 1.7 | 1180 – 1060 | 120 | 225 |
| 9 | 60 | 0.1 | | 32.5 | 0.5 | 2.9 | 2.0 | | 2.0 | 1170 – 1050 | 125 | 230 |

What is claimed is:

1. A gold alloy suitable to have porcelain fired thereon consisting of 60 to 90% gold, 5 to 35% platinum, 0.1 to 3% indium, 0 to 10% palladium, 0 to 3% tin, 0.5 to 3% rhodium, 0.1 to 2% of at least one member of the group consisting of tantalum and tungsten, and 0.3 to 2% zinc, the weight ratio of the platinum group metals to zinc to said member being 15-30:1:0.5-1.3.

2. A gold alloy according to claim 1 wherein said weight ratio is 25:1:1.

3. A gold alloy according to claim 1 which is free of palladium.

4. A gold alloy according to claim 1 which contains at least 1.9% palladium.

5. A gold alloy according to claim 4 free of tin.

6. A gold alloy according to claim 4 containing at least 0.6% tin.

7. A gold alloy according to claim 1 free of tin.

8. A gold alloy according to claim 1 containing at least 0.6% tin.

9. A gold alloy according to claim 1 wherein said member is tantalum.

10. A gold alloy according to claim 1 wherein said member is tungsten.

11. A gold alloy according to claim 1 wherein said member is a mixture of tungsten and tantalum, the mixture containing 20 to 50% tungsten.

* * * * *